United States Patent [19]
Sukata et al.

[11] Patent Number: 5,518,852
[45] Date of Patent: May 21, 1996

[54] NEGATIVE CHARGE CONTROL AGENT AND TONER FOR DEVELOPING ELECTROSTATIC IMAGE

[75] Inventors: Kazuaki Sukata, Kyoto; Shun-ichiro Yamanaka; Shuji Sugawara, both of Osaka, all of Japan

[73] Assignee: Orient Chemical Industries, Ltd., Osaka, Japan

[21] Appl. No.: 349,611

[22] Filed: Dec. 5, 1994

[30] Foreign Application Priority Data

Dec. 8, 1993 [JP] Japan ................................. 5-340851

[51] Int. Cl.$^6$ ................................. G03G 9/097
[52] U.S. Cl. ................................. 430/110
[58] Field of Search ................ 556/442; 430/110, 430/45

[56] References Cited

U.S. PATENT DOCUMENTS

| | | |
|---|---|---|
| 3,576,025 | 4/1971 | Frye . |
| 5,188,929 | 2/1993 | Ishii . |

FOREIGN PATENT DOCUMENTS

| | | | |
|---|---|---|---|
| 61-212852 | 9/1986 | Japan | 430/110 |
| 5-150555 | 6/1993 | Japan | 430/110 |
| 5-150556 | 6/1993 | Japan | 430/110 |
| 5-165255 | 7/1993 | Japan | 430/110 |
| 6-83113 | 3/1994 | Japan | 430/110 |

OTHER PUBLICATIONS

*Organometallics*, vol. 13, No. 5, pp. 1617–1623, by Tacke et al.

Excerpt from Patent Abstracts of Japan, vol. 17, No. 673, publication No. JP5224465, dated Mar. 9, 1993, Inventor Suwa Yoshihito.

*Primary Examiner*—Christopher D. Rodee
*Attorney, Agent, or Firm*—McGlew and Tuttle

[57] ABSTRACT

A negative charge control agent whose active ingredient is an organic silicon complex compound represented by the following formula [I]:

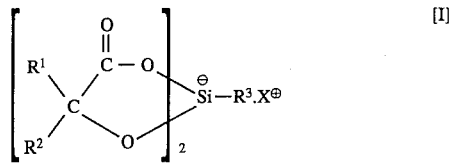

wherein $R^1$ and $R^2$ independently represent hydrogen; or a substituted or unsubstituted alkyl group, cycloalkyl group, aryl group or aralkyl group, $R^3$ represents hydrogen or a substituted or unsubstituted alkyl group, cycloalkyl group, aryl group or aralkyl group, $X^+$ represents an inorganic or organic cation, at least one of $R^1$ and $R^2$ is a substituted or unsubstituted aryl group is usable in a toner for developing an electrostatic image that also contains a coloring agent and a resin.

5 Claims, No Drawings

NEGATIVE CHARGE CONTROL AGENT AND TONER FOR DEVELOPING ELECTROSTATIC IMAGE

BACKGROUND OF THE INVENTION

1. Field of the Invention

The present invention relates to a toner for developing electrostatic latent images in electrophotography, electrostatic recording, electrostatic printing, etc. and a charge control agent for negative charging capable of controlling or stabilizing the amount of charges of the toner, i.e., a negative charge control agent.

2. Description of the Prior Art

In copying machines etc. based on electrophotography, various dry or wet toners containing a coloring agent, a fixing resin and other substances are used to visualize the electrostatic latent image formed on the photoreceptor having a light-sensitive layer containing an inorganic or organic photoconductive substance.

The chargeability of such toners is one of the most important factors in electrostatic latent image developing systems. Thus, to appropriately control or stabilize the amount of charges of the toner, a charge control agent providing a positive or negative charge is often added to the toner.

Examples of conventional charge control agents providing a positive charge for toners include basic dyes, such as nigrosine dyes and triarylmethane dyes, and electron-donating substances, such as quaternary ammonium salts. Examples of conventional charge control agents providing a negative charge for toners include 2:1 metal complex salt azo dyes.

However, many of charge control agents having a dye structure are usually of complex structure, lacking stability, and are likely to decompose or deteriorate to lose their charge control property due to mechanical friction and impact, temperature and humidity changes, electric impact, light irradiation, etc. Such charge control agents lack versatility for color toner use, because they are colored.

Negative charge control agents offering a solution to these problems include chelate compounds with salicylic acid, alkylsalicylic acid, oxynaphthoic acid, salicylaldehyde, phthalic acid, or the like, as a ligand (e.g., Cr, Zn or Al complex of salicylic acid or alkylsalicylic acid, boron complex of salicylic acid, Cr complex of oxynaphthoic acid, Cr or Co complex of salicylaldehyde, Cr or Fe complex of phthalic acid). Although many of these charge control agents of complex structure are of light color, they are not necessarily satisfactory for use in color toners, their resin dispersibility and charge control property stability remain to be improved.

The object of the present invention is to provide a negative charge control agent which is excellent in charge control property, environmental resistance (charge control property stability to changes in temperature and humidity), storage stability (charge control property stability over time) and durability (charge control property stability during multiple repeated use of toner), which is versatile for use in various color toners and achromatic toners, and which is very safe to the human body, and a toner for developing electrostatic images that is excellent in charge control property, environmental resistance, storage stability and durability, and that can be used for various chromatic or achromatic colors.

SUMMARY OF THE INVENTION

The present inventors found that specific complex compounds (complexes) obtained by reaction of a glycolic acid derivative and an organic silicon compound, are very safe to the human body, are excellent in charge control property, environmental resistance, storage stability and durability, and show almost no color tone failure in toner images even when they are incorporated in various chromatic or achromatic toners.

Accordingly, the active ingredient of the negative charge control agent of the present invention is an organic silicon complex compound represented by the following general formula [I]:

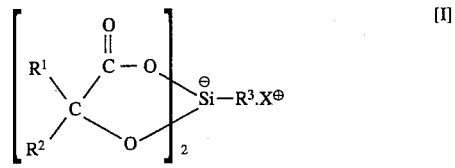

wherein $R^1$ and $R^2$ independently represent hydrogen; or a substituted or unsubstituted alkyl group, cycloalkyl group, aryl group or aralkyl group, $R^3$ represents hydrogen or a substituted or unsubstituted alkyl group, cycloalkyl group, aryl group or aralkyl group, $X^+$ represents an inorganic or organic cation, at least one of $R^1$ and $R^2$ is a substituted or unsubstituted aryl group.

Also, the toner of the present invention for developing electrostatic images comprises at least one negative charge control agent whose active ingredient is an organic silicon complex compound represented by general formula [I], a coloring agent and a resin. Thus, the toner of the present invention may contain one or more kinds of the organic silicon complex compound represented by general formula [I] as the above described negative charge control agent.

The negative charge control agent of the present invention is highly dispersible in resin, and is excellent in charge control property, environmental resistance, storage stability and durability. In addition, its active ingredient, an organic silicon complex compound, is very safe to the human body, and it causes almost no color tone failure in toner images even when used in various chromatic or achromatic toners, because it is substantially colorless.

Also, containing the inventive negative charge control agent, the toner of the present invention for developing electrostatic images is excellent in charge control property, environmental resistance, storage stability and durability, and causes almost no color tone failure in toner images even when used for various chromatic or achromatic toners.

DETAILED DESCRIPTION OF THE INVENTION

Examples of $R^1$ and $R^2$ in the above formula [I] include hydrogen;

substituted or unsubstituted alkyl groups and cycloalkyl groups such as methyl, ethyl, propyl, isopropyl, butyl, isobutyl, sec-butyl, tert-butyl, amyl, isoamyl, octyl, dodecyl and cyclohexyl, which is unsubstituted or substituted by a halogen, preferably fluorine;

substituted or unsubstituted phenyl groups and naphthyl groups (e.g., phenyl, tolyl, 2,5-xylyl, 4-tert-butylphenyl, 3,5-di-tert-butylphenyl, 4-cyanophenyl, 4-bromophenyl, 3-vinylphenyl, 4-nitrophenyl, 4-hydroxyphenyl, biphenyl, naphthyl and tert-butylnaphthyl,) which may be substituted by a linear or branched alkyl group, an alkoxy group such as methoxy or ethoxy, a halogen, a cyano group, a nitro group, a vinyl group, a phenyl group, a hydroxyl group, or the like; and substituted or unsubstituted aralkyl groups such as benzyl, phenethyl, α-methylbenzyl and α, α'-dimethylbenzyl.

$R^3$ is exemplified by substituents in the organic silicon compound described below, specifically the same substituents as those mentioned for $R^1$ and $R^2$ above. Examples of preferable groups for $R^3$ include substituted or unsubstituted aryl groups such as phenyl and tolyl; linear or cyclic alkyl groups such as methyl, ethyl, octyl and cyclohexyl; and aralkyl groups such as benzyl, phenethyl, α-methylbenzyl and α, α'-dimethylbenzyl.

$X^+$ is an inorganic or organic cation having a valency necessary to neutralize the charge specified by the mother component (anionic component) of the compound.

Such cations include hydrogen-ion; ions of alkali metals such as sodium and potassium;

ions of alkaline earth metals such as magnesium, calcium and barium;

ammonium ions of aliphatic primary or secondary amines having 3 to 18 carbon atoms (examples of the primary or secondary amines include n-butylamine, tert-butylamine, amylamine, dibutylamine, isoamylamine, pentylamine, hexylamine, octylamine, 2-ethylhexylamine, dodecylamine, cyclohexylamine, dicyclohexylamine, butoxypropylamine which is interrupted or not interrupted by oxygen, octoxypropylamine which is interrupted or not interrupted by oxygen); ammonium ions of tertiary amines having 3 to 20 carbon atoms (examples of the tertiary amines include N,N-dimethylbenzylamine, triethylamine), quaternary ammonium ions (examples of the quaternary ammonium include tetramethylammonium, trimethylbenzylammonium); ammonium ions of aliphatic diamines (e.g., hexamethylenediamine, N,N-dibutylaminopropylamine); and pyridinium ions. Of these cations, alkali metal ions, ammonium ions of aliphatic amines having 4 to 12 carbon atoms, and ammonium ions of aliphatic diamines are preferred.

The ligand for the organic silicon complex compound represented by general formula [I] above may be a glycolic acid derivative defined by the following formula:

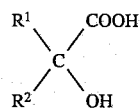

wherein $R^1$ and $R^2$ have the same definitions as those defined for general formula [I] above.

Examples of preferable glycolic acid derivatives include benzyl acid (diphenylglycolic acid) and mandelic acid (phenylglycolic acid).

Examples of silicon donors which can be used to synthesize the organic silicon complex compound represented by general formula [I] above include organic silicon compounds such as phenyltrimethoxysilane, phenyltriethoxysilane, methyltrimethoxysilane, octyltrimethoxysilane, cyclohexyltrimethoxysilane and benzyltrimethoxysilane, with preference given to phenyltrimethoxysilane.

Organic silicon complex compounds represented by general formula [I] can be synthesized in accordance with the method described by C. L. Frye in the Journal of the American Chemical Society, 92, 1205 (1970). Some examples of its synthesis are given below.

SYNTHESIS EXAMPLE 1

A mixture of 2.28 g (10 mmol) of benzyl acid, 0.99 g (5 mmol) of phenyltrimethoxysilane, 1 g (14 mmol) of n-butylamine and 10 ml of methanol was refluxed for 2 hours.

After the solvent was distilled off, acetone-carbon tetrachloride was added to cause recrystallization. The resulting mixture was filtered; the cake was dried to yield 2.05 g of a white powder (Example Compound 1, yield:64.9%) having a melting point of 145°–154° C.

SYNTHESIS EXAMPLE 2

The same procedure as in Synthesis Example 1 was followed, except that benzyl acid was replaced by mandelic acid [1.52 g (10 mmol)], to yield 0.62 g of a white powder (Example Compound 2, yield:25.8%) having a melting point of 107°–112° C.

SYNTHESIS EXAMPLE 3

The same procedure as in Synthesis Example 1 was followed, except that n-butylamine was replaced by hexamethylenediamine [0.6 g (5.2 mmol)], to yield 2.64 g of a white powder (Example Compound 3, yield:85.5%) having a melting point of 147°–152° C.

SYNTHESIS EXAMPLE 4

The same procedure as in Synthesis Example 1 was followed, except that n-butylamine was replaced by sodium methoxide [0.55 g (10 mmol)], to yield 0.84 g of a white powder (Example Compound 4, yield:29.6%) having a melting point of 72°–79° C.

Examples of organic silicon complex compounds represented by general formula [I] (Example Compounds 1–15) are given below, but are not intended to limit the present invention. All these examples are preferably usable as negative charge control agents.

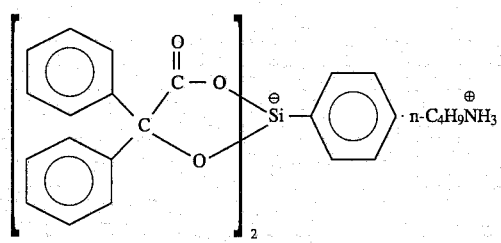

(1)

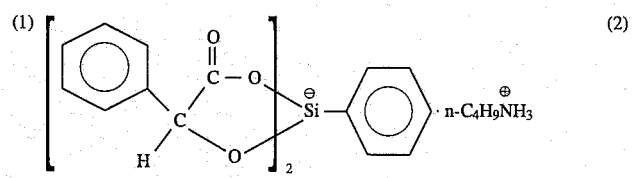

(2)

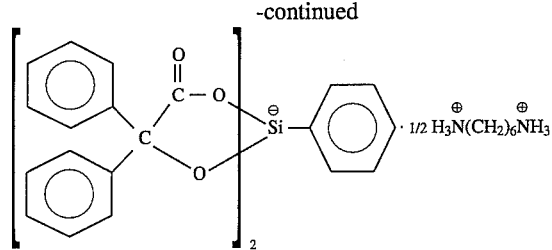
(3)
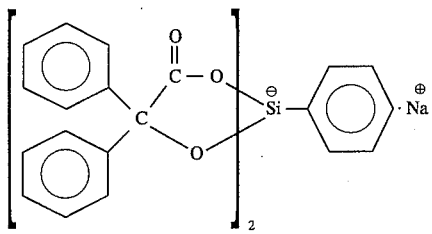
(4)
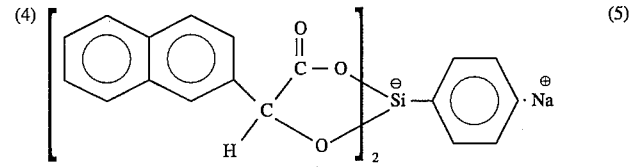
(5)
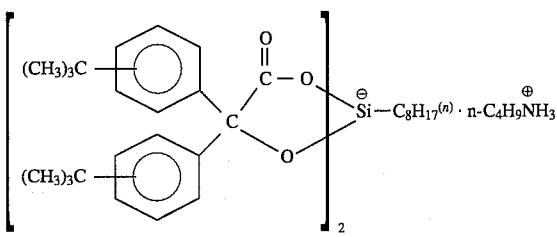
(6)
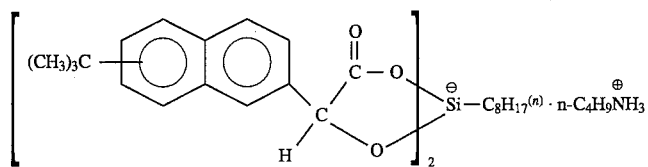
(7)
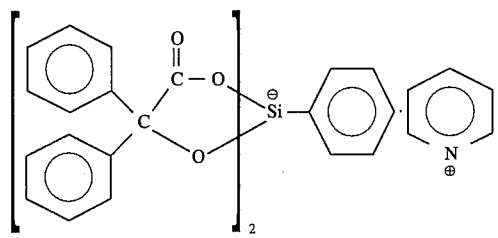
(8)
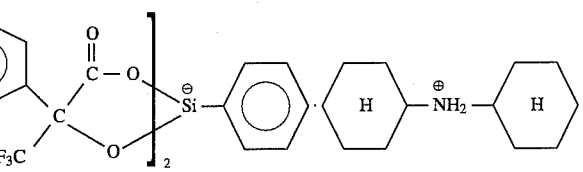
(9)
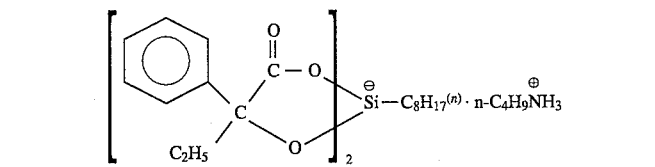
(10)
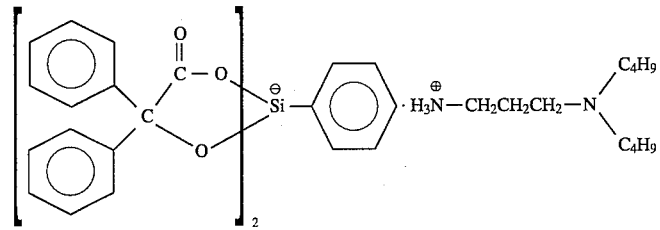
(11)
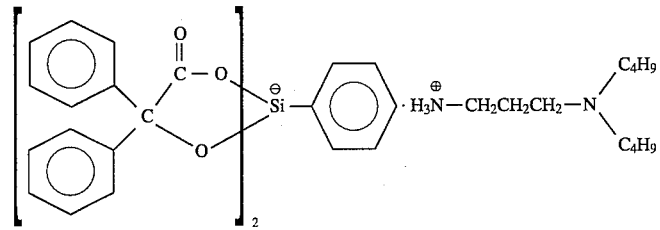

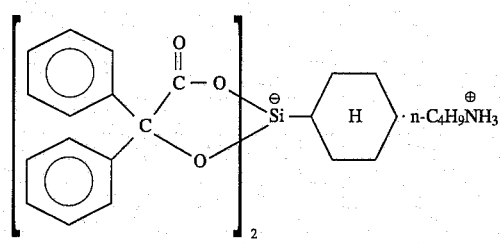

(12)

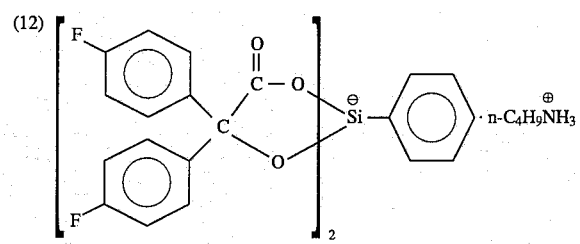

(13)

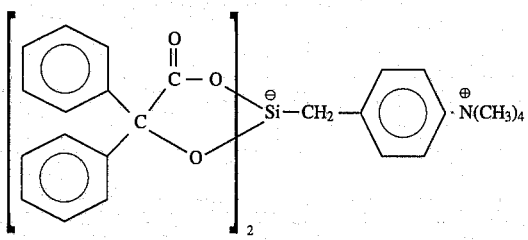

(14)

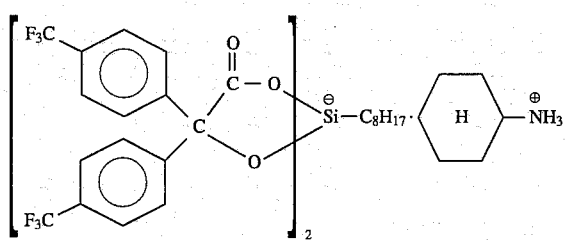

(15)

The toner of the present invention for developing electrostatic images desirably contains an organic silicon complex compound as the negative charge control agent of the present invention in a ratio of 0.1 to 10 parts by weight per 100 parts by weight of resin. A more preferable content of the organic silicon complex compound is 0.5 to 5 parts by weight per 100 parts by weight of resin.

Also, to improve toner quality, additives such as electroconductive grains, fluidity improving agents and image peeling preventing agents may be added internally or externally to the toner of the present invention for developing electrostatic images.

Examples of resins used in the toner of the present invention include the following known resins or binder resins for use in toners. Specifically, styrene resin, styrene-acrylic resin, styrene-butadiene resin, styrene-maleic acid resin, styrene-vinyl methyl ether resin, styrene-methacrylic acid ester copolymer, phenol resin, epoxy resin, polyester resin, polypropylene resin and paraffin wax may be mentioned as examples. These resins may be used singly or in combination.

The toner of the present invention may incorporate various known dyes and pigments as coloring agents. Examples of such dyes and pigments include organic pigments such as quinophthalone yellow, isoindolinone yellow, perillene orange, perillene maroon, rhodamine 6G lake, quinacridone red, anthanthrone red, rose bengale, copper phthalocyanine blue, copper phthalocyanine green and diketopyrrolopyrrole pigments, and inorganic pigments such as carbon black, titanium white, titanium yellow, ultramarine, cobalt blue and red iron oxide. Examples of preferable coloring agents for color toner use include various oil-soluble dyes or disperse dyes, such as azo dyes, quinophthalone dyes, anthraquinone dyes, phthalocyanine dyes, indophenol dyes and indoaniline dyes, and triarylmethane dyes and xanthene dyes modified with a resin such as rosin, rosin-modified phenol or maleic acid.

The toner of the present invention for developing electrostatic images may incorporate the above-mentioned coloring agents singly or in combination. Dyes and pigments having a good spectral property can be preferably used to prepare a toner of the three primaries for full-color imaging. Chromatic monocolor toners may incorporate an appropriate combination of a pigment and dye of the same color tone, such as a quinophthalone pigment and dye, a xanthene or rhodamine pigment and dye, or a phthalocyanine pigment and dye, as a coloring agent.

The toner of the present invention for developing electrostatic images is, for example, produced as follows:

A dry negatively chargeable toner having an average particle size of 5 to 20 μm can be prepared by thoroughly mixing a resin and coloring agent as described above, the charge control agent of the present invention, and, if necessary, a ferromagnetic material, a fluidizing agent and other additives, using a ball mill or another mechanical mixer, subsequently kneading the mixture in a molten state using a hot kneader, such as a heat roll, kneader or extruder, cooling and solidifying the mixture, and then pulverizing the mixture and classifying the particles.

Other applicable methods include the method in which the starting materials are dispersed in a binder resin solution, followed by spray drying, and the polymerizing toner production method in which a given set of starting materials are mixed with a monomer for binder resin to yield an emulsified suspension which is then polymerized to yield the desired toner.

When using the toner of the present invention as a two-component developer, development can be achieved by the two-component magnetic brush developing process or another process, using the toner in mixture with carrier powder.

Any known carrier can be used. Examples of the carrier include iron powder, nickel powder, ferrite powder and glass beads of about 50 to 200 μm in particle size, and such materials as coated with acrylic acid ester copolymer, styrene-acrylic acid ester copolymer, styrene-methacrylic acid ester copolymer, silicone resin, polyamide resin, ethylene fluoride resin, or the like.

When using the toner of the present invention as a one-component developer, an appropriate amount of fine powder of a ferromagnetic material, such as iron powder, nickel powder or ferrite powder, may be added and dispersed in preparing the toner as described above. Examples of developing processes which can be used in this case include contact development and jumping development.

EXAMPLES

The present invention is hereinafter described in more detail by means of the following examples, but the invention is never limited by these examples. In the description below, "part(s) by weight" are referred to as "part(s)" for short.

EXAMPLE 1

Polyester resin [HP-301 (trade name), produced by The Nippon Synthetic Chemical Industry, Co., Ltd.] ... 100 parts Low polymer polypropylene [Biscal 550P (trade name), produced by Sanyo Kasei Co., Ltd.] ... 5 parts Copper phthalocyanine dye [Valifast Blue 2606 (trade name), produced by Orient Chemical Industries Ltd.] ... 2 parts Copper phthalocyanine pigment ... 3 parts Example Compound (1) (negative charge control agent) ... 2 parts The above ingredients were uniformly pre-mixed using a high-speed mixer, and then kneaded in a molten state using an extruder, cooled, and roughly milled in a vibration mill. The obtained coarse product was finely pulverized using an air jet mill equipped with a classifier to obtain a negatively chargeable cyan toner of 10 to 20 μm in particle size.

5 parts of this toner was admixed with 95 parts of an iron powder carrier [TEFV 200/300 (trade name), produced by Powdertech Co., Ltd.] to yield a developer.

This developer was found to be $-15.1°$ C./g in the amount of initial blowoff charge. The amounts of initial blowoff charges of this developer under low-temperature low-humidity conditions (5° C., 30% relative humidity) and high-temperature high-humidity conditions (35° C., 80% relative humidity) were $-15.1$ μC/g and $-15.3$ μC/g, respectively, indicating very high environmental stability. The storage stability of the developer was also good.

When this developer was used for a commercial copying machine to take multiple copies, high-quality images, without image density reduction, fogging, color tone failure, etc., were obtained, demonstrating good charge stability and retention.

EXAMPLE 2

The same procedure as in Example 1 was followed, except that the negative charge control agent was replaced with Example Compound (2) as obtained in Synthesis Example 2, to yield a toner and a developer, which were then evaluated; excellent results were obtained as in Example 1.

EXAMPLE 3

Polyester resin [HP-301 (trade name), produced by The Nippon Synthetic Chemical Industry, Co., Ltd.] ... 100 parts Low polymer polypropylene [Biscal 550P (trade name), produced by Sanyo Kasei Co., Ltd.] ... 5 parts Rhodamine dye [Oil Pink 312 (trade name), produced by Orient Chemical Industries Ltd.] ... 3 parts Quinacridone red ... 3 parts Example Compound (3) (negative charge control agent) ... 2 parts The above ingredients were treated in the same manner as in Example 4 to yield a negatively chargeable magenta toner and a developer.

This developer was found to be $-15.0$ μC/g in the amount of initial blowoff charge. The amounts of initial blowoff charges of this developer under low-temperature low-humidity conditions (5° C., 30% relative humidity) and high-temperature high-humidity conditions (35° C., 80% relative humidity) were $-15.0$ μC/g and $-14.8$ μC/g, respectively, indicating very high environmental stability. The storage stability of the developer was also good.

When this developer was used for a commercial copying machine to take multiple copies, high-quality images, without image density reduction, fogging, color tone failure, etc., were obtained, demonstrating good charge stability and retention.

EXAMPLE 4

The same procedure as in Examples 1 and 3 was followed, except that the negative charge control agent was replaced with Example Compound (4) as obtained in Synthesis Example 4, to yield a toner and a developer, which were then evaluated; excellent results were obtained as in Example 3.

EXAMPLE 5

Styrene-acrylic copolymer resin [HIMER SMB600 (trade name), produced by Sanyo Kasei Co., Ltd.] ... 100 parts Low polymer polypropylene [Biscal 550P (trade name), produced by Sanyo Kasei Co., Ltd.] ... 10 parts Carbon black [MA-100 (trade name), produced by Mitsubishi Chemical Industries, Ltd.] ... 5 parts Example Compound (1) (negative charge control agent) ... 2 parts The above ingredients were treated in the same manner as in Example 1 to yield a negatively chargeable black toner and a developer.

This developer was found to be $-15.0$ μC/g in the amount of initial blowoff charge. The amounts of initial blowoff charges of this developer under low-temperature low-humidity conditions (5° C., 30% relative humidity) and high-temperature high-humidity conditions (35° C., 80% relative humidity) were $-15.1$ μC/g and $-14.7$ μC/g, respectively, indicating very high environmental stability and storage stability.

When this developer was used for a commercial copying machine to take multiple copies, high-quality images, without image density reduction, fogging, etc., were obtained, demonstrating good charge stability. The storage stability of the developer was also good.

EXAMPLE 6

Polyester resin [HP-301 (trade name), produced by The Nippon Synthetic Chemical Industry, Co., Ltd.] ... 100 parts Tri-iron tetroxide [EPT-500 (trade name), produced by Toda Kogyo Corporation] ... 40 parts Low polymer polypropylene [Biscal 550P (trade name), produced by Sanyo Kasei Co., Ltd.] ... 10 parts Carbon black [MA-100 (trade name), produced by Mitsubishi Chemical Industries, Ltd.] ... 6 parts Example Compound (2) (negative charge control agent) . . . 2 parts The above ingredients were uniformly pre-mixed using a ball mill to yield a premix, which was then kneaded in a molten state at 180° C. using a twin-screw extruder, cooled and thereafter roughly crushed, finely pulverized and classified to yield a one-component toner of 5 to 15 μm in particle size. When this toner was used for a commercial copying machine to form toner images, fog-free high-quality images with good thin-line reproducibility having a solid portion reflection density of 1.27 were obtained.

COMPARATIVE TEST 1

To compare the actual imaging performance, a cyan toner and a developer were prepared and used to form toner images in the same manner as in Example 1, except that the negative charge control agent was replaced with a borodibenzylate compound (described in Japanese Patent Unexamined Publication No. 224465/1993). The obtained color reproducibility was as excellent as in Example 1, but the developer lacked charging performance stability and durability.

COMPARATIVE TEST 2

A magenta toner was prepared and evaluated in the same manner as in Example 3, except that Example Compound (3) was not used. Since image scattering, disturbance, fogging, etc. occurred, the toner was adjudged inappropriate.

What is claimed is:

1. Toner for developing an electrostatic image, comprising a toner resin, a coloring agent and a negative charge control agent comprising an organic silicon complex compound of the formula [I]:

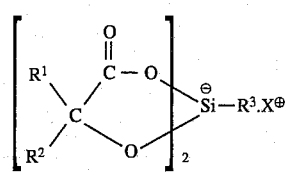

wherein $R^1$ and $R^2$ independently represent hydrogen or a substituted or unsubstituted alkyl group, cycloalkyl group, aryl group or aralkyl group, $R^3$ represents hydrogen or a substituted or unsubstituted alkyl group, cycloalkyl group, aryl group or aralkyl group, $X^+$ represents an inorganic or organic cation, at least one of $R^1$ and $R^2$ being a substituted or unsubstituted aryl group.

2. Toner of claim 1 wherein the organic silicon complex compound is contained in a ratio of about 0.1 to 10 parts by weight per 100 parts by weight of the resin.

3. Toner of claim 1 wherein $R^3$ represents a member of the group consisting of a substituted or unsubstituted aryl group, a linear or cyclic alkyl group, and an aralkyl group.

4. Toner of claim 1 wherein $R^3$ represents a member of the group consisting of phenyl, tolyl, methyl, ethyl, octyl, cyclohexyl, benzyl, phenethyl, α-methylbenzyl and α,α'-dimethylbenzyl.

5. Toner of claim 1 wherein $X^+$ represents a cation selected from the group consisting of an alkali metal ion, an ammonium ion of an aliphatic amine having 4 to 12 carbon atoms, and an ammonium ion of an aliphatic diamine.

* * * * *